United States Patent [19]
Misra et al.

[11] Patent Number: 5,869,098
[45] Date of Patent: Feb. 9, 1999

[54] FAST-DISSOLVING COMESTIBLE UNITS FORMED UNDER HIGH-SPEED/HIGH-PRESSURE CONDITIONS

[75] Inventors: Tushar K. Misra, Leesburg; Jeffery W. Currington, Winchester; Satish V. Kamath, Centreville; Pradeep P. Sanghvi, Herndon; John R. Sisak; Michael G. Raiden, both of Fairfax, all of Va.

[73] Assignee: Fuisz Technologies LTD., Chantilly, Va.

[21] Appl. No.: 915,067

[22] Filed: Aug. 20, 1997

[51] Int. Cl.⁶ ..................................................... A61K 31/74
[52] U.S. Cl. ........................... 424/484; 424/488; 424/465; 424/493; 424/490; 424/489
[58] Field of Search ..................................... 424/489, 490, 424/493, 484, 488, 465

[56] References Cited

U.S. PATENT DOCUMENTS

| | | | |
|---|---|---|---|
| 5,646,131 | 7/1997 | Badwan | 514/58 |
| 5,683,720 | 11/1997 | Myers et al. | 424/489 |
| 5,686,094 | 11/1997 | Acharya | 424/434 |

FOREIGN PATENT DOCUMENTS 0 636 364 A1  1/1995  European Pat. Off. ......... A61K 9/20

*Primary Examiner*—Thurman K. Page
*Assistant Examiner*—D. Faulkner
*Attorney, Agent, or Firm*—Sandra M. Nolan

[57] ABSTRACT

The invention relates to compositions useful for making tablets which can be formed using conventional tableting machines and which disintegrate rapidly when placed in the mouth. The compositions typically include partially hygroscopic shearform matrices which may be recrystallized using crystallization promoters.

15 Claims, No Drawings

5,869,098

FAST-DISSOLVING COMESTIBLE UNITS FORMED UNDER HIGH-SPEED/HIGH-PRESSURE CONDITIONS

FIELD OF THE INVENTION

The invention deals with compositions having enhanced cohesive and self-binding properties which permit tableting without added glycerine. Tablets made herewith disintegrate rapidly when placed in the mouth.

RELATED APPLICATIONS

This invention is related to: U.S. patent application Ser. No. 08/915,068 filed Aug. 20, 1997 and entitled SELF-BINDING SHEARFORM COMPOSITIONS; provisional U.S. patent application Ser. No. 60/056,617 filed Aug. 20, 1997; and U.S. patent application Ser. No. 08/914,972, also filed Aug. 20, 1997 entitled PROCESS FOR IMPROVING FLOW AND COMPRESSION OF TABLETING COMPOSITIONS.

BACKGROUND OF THE INVENTION

Glycerine, a tableting additive, has been used for its ability to lend stickiness to tablet formulations. Some stickiness is desirable, serving to provide cohesion to hold the tablet ingredients together during compression. However, in certain situations, the use of glycerine can produce too much stickiness, resulting in the formulations clumping or sticking in various machine parts before and during tableting. Self-binding, readily flowable compositions containing no glycerine have been unknown to the art.

One method for addressing the need for self-binding flowable formulations was the production of shearform matrices or flosses. These matrices result when using certain processing techniques, such as the following:

U.S. Pat. No. 5,587,172, incorporated herein by reference, discusses the use of flash heat techniques to produce sucrose-containing shearform flosses, which are then processed to yield quick-dissolving tablets.

The use of shearform matrices for forming comestible units is described in co-assigned and co-pending PCT application No. PCT/US95/07144, filed Jun. 6, 1995. The PCT case discloses a quick dissolving tablet which is formed by: (1) using flash-flow technology to provide a shearform matrix; (2) combining the partially recrystallized matrix with an additive to form flowable, compactible particulate blends; and (3) compacting the blends at relatively low pressure to form comestible units, such as tablets.

Additionally, PCT publication WO 95/34293 (published Dec. 21, 1995) from co-assigned PCT Application No. PCT/US95/07194, filed Jun. 6, 1995, discloses a process and apparatus for making rapidly dissolving dosage units by flash-flow processing. In this PCT application, a shearform matrix is formed by the flash-flow process, the shearform matrix is combined with an additive, and the matrix is molded to make a unit dosage form. Tamping may be used to compact the dosage form and increase its integrity.

While the use of shearform matrices is an advance in the art, there still exists a need for non-sticking tabletable compositions which, when molded, yield fast-dissolving dosage units. This invention addresses that need.

SUMMARY OF THE INVENTION

The invention provides compositions and dosage units having improved properties and methods of making them.

Co-owned U.S. patent application Ser. No. 08/915,068, entitled SELF-BINDING SHEARFORM COMPOSITION and filed concurrently herewith, describes tablet formulations derived from saccharide-based carriers in which the use of a unique combination of feedstock ingredients yields self-binding, flowable matrices and tablet compositions. This combination—which employs a blend of sugar alcohols, i.e., sorbitol and xylitol—is superior to glycerine in providing cohesive properties and flowability.

Applicants have discovered that tablet compositions derived from partially hydroscopic matrices containing these sugar alcohols are useful—in the presence of tableting aids and crystallization promoters—in both high- and low-pressure tableting processes. Tablets therefrom rapidly dissolve when placed in the mouth, generally in less than 30 seconds.

The tablet compositions of the invention are based on matrices which comprise at least one sugar alcohol, which matrices fall into one of the following groups:

One group—called "single floss" or "unifloss" systems—is exemplified by a shearform matrix, or floss, containing a carrier and two or more sugar alcohols, one of which is xylitol.

A second group—termed "dual floss"—is exemplified by (I) a first shearform carrier matrix (the "base floss") comprising a carrier and at least one sugar alcohol, generally sorbitol; and (II) a second shearform binder matrix (the "binder floss") comprising a carrier and xylitol.

Actives and other conventional tablet ingredients can be added, in suitable amounts, to the compositions of the present invention during the production of the matrices and/or after the matrices are collected and chopped, but before tableting.

DETAILED DESCRIPTION OF THE INVENTION

Unless otherwise stated, the parts and percentages used in the specification are weight percentages, based upon total composition weight. The terms "matrix" and "floss" are used interchangeably.

The applicants have found that by using a combination of ingredients and process, dissolve in the mouth tablets can be produced using conventional tableting equipment. In addition, even though pressures from about 500 psi to about 10,000 psi or higher can be used on the inventive composition, the dissolution time, in the mouth, for tablets made from this composition is in the range from about 3 seconds to 30 seconds. Prior compositions required the use of specialized, low-pressure (less than 1000 psi) tableting equipment.

Additionally, it is now possible to prepare a tabletable composition, containing an active agent, with sufficient "flow" characteristics and properties to enable one to transport the composition to and through conventional tableting equipment using gravity, forced air or vacuum. This composition can then be compacted under a wide range of tableting.

The preparation of flosses suitable for use in the present invention is disclosed in co-assigned patent applications PCT application No. PCT/US95/07144, filed Jun. 6, 1995, and PCT publication WO 95/34293, both incorporated herein by reference. Preferably, the floss is a "shearform matrix" produced by subjecting a feedstock which contains a sugar carrier to flash-heat processing.

In the flash-heat process, the feedstock is simultaneously subjected to centrifugal force and to a temperature gradient which raises the temperature of the mass to create an internal flow condition which permits part of it to move with respect to the rest of the mass. The flowing mass exits through openings provided in the perimeter of a spinning head. The temperature gradient is supplied using heaters or other means which cause the mass' temperature to rise. Centrifugal force in the spinning head flings the internally flowing mass outwardly, so that it reforms as discrete fibers with changed structures.

An apparatus which produces suitable conditions is a modified floss making machine, such as that described in U.S. patent application Ser. No. 08/854,344 filed on May 12, 1997, entitled APPARATUS FOR MELT SPINNING FEEDSTOCK MATERIAL HAVING A FLOW RESTRICTING RING. The content of that application is incorporated herein by reference.

Spinning is typically conducted at temperatures and speeds of about 150° C. to 250° C. and 3,000 to 5,000 rpm, respectively. Suitable spinner heads include that disclosed in U.S. Pat. No. 5,458,823, assigned to Applicants' assignee, which is hereby incorporated by reference.

Other apparatuses and processes which provide similar forces and temperature gradient conditions can be used.

The matrices used herein include, as feedstock ingredients, carrier materials, which carriers comprise at least one ingredient selected from materials which are capable of undergoing the physical and/or chemical changes associated with flash heat processing. Useful carriers include carbohydrates which become free-form particulates when flash heat processed. Saccharide-based carriers, including saccharides (i.e., sugars), polysaccharides and mixtures thereof can be also used.

The feedstocks used in the invention can include carriers chosen from various classes of "sugars." "Sugars" are those substances which are based on simple crystalline mono- and di-saccharide structures, i.e., based on $C_5$ and $C_6$ sugar structures. They may include glucose, sucrose, fructose, lactose, maltose, pentose, arbinose, xylose, ribose, mannose, galactose, sorbose, dextrose and sugar alcohols, such as sorbitol, mannitol, xylitol, maltitol, isomalt, sucralose and the like and mixtures thereof. Sucrose is the preferred sugar.

Useful mixtures of carriers include the sugars listed above along with additional mono- di-, tri- and polysaccharides. Additional saccharides can be used in amounts of up to 50% by weight, preferably up to 30%, most preferably up to 20%, of the total carbohydrate content.

Optionally, the polysaccharides can be used alone as carriers. Polysaccharide carriers include polydextrose and the like. Polydextrose is a non-sucrose, essentially non-nutritive, carbohydrate substitute. It can be prepared through polymerization of glucose in the presence of polycarboxylic acid catalysts and polyols. Generally, polydextrose is commercially available in three forms: polydextrose A and polydextrose K, which are powdered solids; and polydextrose N supplied as a 70% solution. Applicants incorporate by reference herein the contents of U.S. Pat. No. 5,501,858, which discusses polydextrose.

If other carrier materials are used, they are employed in combination with sugar and not as total replacement therefor. For example, maltodextrins may be employed. Maltodextrins include mixtures of carbohydrates resulting from the hydrolysis of a saccharide. They are solids having a dextrose equivalent (DE) of up to and including 65.

The carrier can also include maltooligo-saccharides produced by selective hydrolysis of corn starch. A general description of maltooligo-saccharides useful herein is set forth in co-owned U.S. Pat. Nos. 5,347,431 and 5,429,836, both incorporated herein by reference.

Applicants typically use the following systems of matrices, which systems are devoid of glycerine.

In the first system, xylitol is added to a mixture of saccharide-based carrier and one or more additional sugar alcohols, with sorbitol being favored as an added sugar alcohol. The carrier mix is flash-heat processed to provide a shearform floss having self-binding properties. Flosses made using sucrose, sorbitol and xylitol have been found to yield particularly effective self-binding properties. They exemplify "single floss" or "unifloss" systems.

The second system makes separate xylitol-containing binder flosses. The binder flosses ("binder portions") are combined with base flosses ("base portions"), which contain a different sugar alcohol and a saccharide. Preferably, the base floss contains sorbitol and sucrose, while the binder floss contains xylitol and possibly sorbitol. These are termed "dual floss" systems.

The ingredients which increase cohesiveness and give self-binding properties preferably include sugar alcohols, such as sorbitol, xylitol, maltitol, mannitol and mixtures thereof, all of which form flosses. Other sugar alcohols, especially hygroscopic ones, are contemplated.

Xylitol and sorbitol are the preferred sugar alcohols. Effective amounts of xylitol in the flosses are between about 0.5% and 25%, and preferably about 10% by weight. Sorbitol is used in the flosses in amounts of about 0.5% to about 40%.

When sorbitol and xylitol are used, the ratio of sorbitol to xylitol is from about 1:0.1 to about 1:10.

In dual floss systems, about 20 to about 80%, preferably about 34%, of the total floss content is xylitol-containing, or binder, floss. Likewise, the sorbitol-containing, or base, floss may be about 20 to 80% of the total floss. In some "dual floss" embodiments, xylitol-containing flosses are first mixed with active ingredient(s), then mixed with sucrose/sorbitol flosses.

Regardless of the number of flosses, the total floss content preferably includes about 50 to about 85% sucrose, about 5 to about 20% sorbitol and about 5% to about 25% xylitol.

In some cases, flosses are used along with bio-affecting, or active agents in the form of microsphere granulates or crystalline particles in the tableting process. It is preferred that the bio-affecting agent be coated as well. Often, a xylitol-containing floss is added to microspheres of one or more active agents first and then a non-xylitol-containing floss is added. Typically, the weight ratio of total floss to microspheres is about 1:1. In these instances, about 5% to about 25% of the floss is xylitol.

The amorphous shearform matrix of the present invention is preferably made from a feedstock which includes sucrose, sorbitol, and xylitol. As set forth in a co-assigned application entitled "SELF-BINDING SHEARFORM COMPOSITIONS," Attorney Docket No. 0013.US, filed concurrently herewith, these compositions have superior cohesiveness. In addition, the matrices, when partially recrystallized, yield matrix-containing mixes having particulate flowability such that they are suitable for use in high-speed and high-pressure tableting equipment to yield fast-dissolving tablets.

Applicants do not wish to be bound by a particular theory; however, they believe that a hygroscopic material must be present in the matrices and the matrices must be partially crystallized to provide good self-binding and flow characteristics to the compositions containing them.

Applicants theorize that the hygroscopic material is initially present in the matrix in its amorphous state, but, due to its propensity to pick up moisture, it recrystallizes into a more crystalline structure. When sufficient recrystallization has occurred in the matrice as a whole, flowability is enhanced and the composition can be tabled on conventional tableting machines.

The compositions to be processed into comestible, or dosage units generally contain conventional tableting additives. Conventional quantities of same may be incorporated into one or more of the matrices or may be mixed therewith prior to tableting. Useful amounts of conventional additives range from about 0.01% to about 80% by weight, based on the weight of the matrices or formulations in which they are used. The quantities may vary from these amounts, depending on the functions of the additives and the characteristics desired in the matrices and/or the final tablet compositions.

Conventional tableting aids and additives may be selected from a wide variety of materials such as lubricants, glidants, anti-caking agents and flow agents. For example, lubricants such as magnesium stearate, calcium stearate, sodium chloride, zinc stearate, hydrogenated vegetable oils, sterotex, polyoxyethylene, glyceryl monostearate, talc, polyethylene glycol, sodium benzoate, sodium lauryl sulfate, magnesium lauryl sulfate, sodium stearyl fumarate, adipic acid, light mineral oil and the like may be employed, with sodium stearyl fumarate preferred. Waxy fatty acid esters, such as glyceryl behenate, sold as "Compritol" products, can be used. Mixtures are operable.

Lubricants are used in amounts ranging from about 0% to about 10%, with about 0.01% to about 5.0% typically used.

Glidants such as starch, talc, lactose, stearates, dibasic calcium phosphate, magnesium carbonate, magnesium oxide, calcium silicate, Cabosil™, Syloid™, and silicon dioxide aerogels may be employed.

Lactose, which may be a glidant or filler, can be added to the chopped floss at about 2% concentration to inhibit clumping.

Glidants are present in amounts ranging from about 0% to about 20%, with amounts of about 0.1% to about 5.0% being typical.

The preformed matrices produced in accordance herewith are generally rendered more crystalline by one or more of the following crystallizing techniques. The nature of the matrix feedstock determines whether the matrix is to be recrystallized after it is formed. Highly amorphous feedstocks are crystallized. Crystalline ones are recrystallized. Nonetheless, the terms "crystallization" and "recrystallization" are used interchangeably in the following discussion.

The amorphous matrices are typically recrystallized by incorporating into, or contacting them with one or more crystallization promoters, termed "crystallization enhancers" and "crystallization modifiers." Both types of promoters assist in the recrystallization.

One technique for recrystallizing involves the use of crystallization enhancers. These are generally forces or physical materials that are used after the floss has been formed, but before the floss-containing composition is tableted. Suitable crystallization enhancers include ethanol, polyvinylpyrrolidone, water (e.g., moisture), glycerine, radiant energy (e.g., microwaves, heat, etc.) and the like. Combinations can be used. When they involve physical materials, typical amounts of these enhancers range from about 0.01% to about 10.0% by weight of the tablet composition.

Another crystallization technique involves crystallization modifiers. These crystallization modifiers are either (a) floss ingredients used at levels of about 0.01% to about 20.0% by weight of the floss, or (b) a combination of ingredients (a) with environmental agents or forces such as increased moisture and heat. The combination of additives with heat/humidity is called "aging."

Surfactants are preferred crystallization modifiers. Other materials which are non-saccharide hydrophilic organic materials may also be used. Useful modifiers preferably have a hydrophilic to lipid balance (HLB) of about 6 or more. Such materials include, without limitation, anionic, cationic, and zwitterionic surfactants as well as neutral materials with suitable HLB values. Hydrophilic materials having polyethylene oxide linkages are effective. Those with molecular weights of at least about 200, preferably at least 400, are highly useful.

Crystallization modifiers useful herein include: lecithin, polyethylene glycol (PEG), propylene glycol (PPG), dextrose, the SPANS and TWEENS which are commercially available from ICI America, and the surface active agents known as "Carbowax". Generally, the polyoxyethylene sorbitan fatty acid esters called TWEENS, or combinations of such modifiers are used. Crystallization modifiers are usually incorporated into matrices in amounts of between about 0% and 10%.

Whether they are physical materials or forces, crystallization modifiers and/or enhancers are supplied at levels sufficient to give the floss/additive mixes the cohesivity and particular flavorability needed for further processing, e.g., molding into tablets.

The matrices are allowed to recrystallize, with or without added crystallization assistants, i.e., modifiers and enhancers, either before or after they are combined with the non-matrix component(s), e.g., the bio-affecting additives (s). The recrystallization level of the matrix generally reaches at least about 10% before tableting. Crystallization levels of 20% or more are highly effective. The use of partially recrystallized matrices leads to compositions that are free flowing and tabletable using conventional machines. U.S. Pat. No. 5,597,416 describes a process for recrystallizing in the presence of additives.

Methods for effecting the recrystallization of the matrices include one or more of the following: use of Tween 80 or other crystallization modifier(s) in the matrix premix; aging of the matrix for up to several weeks; contacting the matrix with sufficient moisture and heat to induce crystallization; and treating the floss or the floss-containing composition with ethanol, ethanol vapors or another crystallization enhancer. Combinations of these may be used so that the matrices may be contacted with a crystallization enhancer while they are also in contact with moisture or heat.

When a surfactant, such as a Tween, is used, about 0.001% to about 1.00% is included in the floss preblend as a crystallization modifier. Following preblending, the formulations are processed into flosses, then chopped and used, with or without additives, to make tablets. Mixtures of surfactants can be used.

Aging may be used to recrystallize the matrix or floss. The aging process involves a two-step process. First the matrix, optionally containing at least one crystallization modifier, is formed, chopped and allowed to stand in closed or sealed containers without agitation under ambient conditions, e.g., at room temperature and atmospheric pressure, for up to several days, preferably for about 1 to about 3 days. Later, the matrix is mixed, and optionally further chopped, with one or more other ingredients. The mix is then aged by allowing it to stand for an additional period of about 1 to about 3 days. Generally, the two-step aging process takes a total of about one week, with periods of about 4 to about 5 days being typical.

The flosses may also be recrystallized by subjecting them to increased heat and moisture without additives. This process is similar to aging, but involves shorter periods of time. Using a fluidized bed apparatus or other suitable agitating device, chopped floss is fluidized while heating, at ambient humidity and pressure, to a temperature of about 25° C. to about 50° C. Generally, the temperature must be monitored to minimize clumping of floss particles. If any clumping occurs, the floss particles must be sieved before being further processed. Heating times of about 5 to about 30 minutes are typical.

When ethanol is used as a crystallization enhancer it is used in amounts, based upon the weight of the matrix, of about 0.1% to about 10%, with amounts of about 0.5% to about 8.0% being very effective. The preformed matrix is contacted with ethanol. Excess ethanol is evaporated by drying for about an hour at about 85° F. to about 100° F., with 95° F. being highly useful. The drying step is carried out using tray drying, a jacketed mixer or other suitable method. Ethanol vapors may also be used. Following ethanol treatment, the matrix becomes partially recrystallized on standing for a period ranging from about a few hours up to several weeks. When the floss is about 5% to about 30% recrystallized, it is granulated and tableted after blending with other ingredients. The tableting compositions flow readily and are cohesive.

U.S. Pat. No. 5,610,076, incorporated herein by reference, discloses the use of ethanol to promote crystallization of surfactant-containing flosses.

Recrystallization of the matrix may take place in the presence of one or more bio-affecting agents or other additives.

Recrystallization of the matrix can be monitored by measuring the transmittance of polarized light therethrough or by the use of a scanning electron microscope. Amorphous floss or shearform matrix does not transmit polarized light and appears black in the light microscope when viewed with polarized light. Using bright field microscopy or the scanning electron microscope, the surface of the floss appears very smooth. In this condition, it is 0% recrystallized. That is, the floss is 100% amorphous.

Recrystallization of amorphous matrix starts at the surface of the mass and can be modified, e.g., accelerated, by the presence of crystallization modifiers, as well as moisture. When TWEENS assist the recrystallization, initiation of recrystallization is evidenced by a birefringence observed on the surface of the shearform matrix (floss) as viewed with polarized light. There are faint points of light riddled throughout the matrix' surface. When birefringence appears, recrystallization has begun. At this stage, recrystallization is between about 1% and 5%.

As recrystallization proceeds, the birefringence on the surface of the matrix grows continually stronger and appears brighter. The points of light grow in size, number and intensity, seeming to almost connect. Using bright field or scanning electron microscopy, the surface of the matrix appears wrinkled. At this point, about 5 to 10% recrystallization has occurred.

Surfactant (e.g., TWEEN 80) droplets become entrapped within the matrix. These droplets are obscured as recrystallization proceeds. As long as they are visible, the floss is generally not more than about 10% to 20% recrystallized. When they are no longer observable, the extent of recrystallization is no more than about 50%.

The recrystallization of the matrix results in reduction of the total volume of material. Ordered assays of molecules take up less space than disordered arrays. Since recrystallization begins at the surface of the floss, a crust is formed which maintains the size and shape of the floss. There is an increase in the total free volume space within the floss as recrystallization nears completion, which manifests itself as a void inside the floss. This is evidenced by a darkened central cavity in light microscopy and a hollow interior in scanning electron microscopy. At this stage, the floss is believed to be about 50% to about 75% recrystallized.

The intensity of transmitted polarized light increases as the floss becomes more crystalline. The polarized light can be measured by a photon detector and assigned a value against calculated standards on a gray-scale.

The final observable event in the recrystallization of floss is the appearance of fine, "cat whisker-like" needles and tiny blades which grow and project from the surface of the floss. These fine crystals, believed to be sorbitol (cat whiskers) and xylitol (blades), literally cover the floss like a blanket of fuzz. These features can be easily recognized by both light and electron microscopes. Their appearance indicates the final stage of recrystallization. The floss is now 100% recrystallized, i.e., substantially non-amorphous.

The matrix portions of the tabletable composition are typically formed via flash-heat processing into a floss. The strands of the floss are macerated or chopped into rods for further processing. The rods of chopped floss have lengths of about 50 to about 500 microns.

When active agents, such as bio-affecting agents, are added, they are often added in the form of particles, and generally as uniform coated microspheres. Suitable microspheres and other spheroidal particles can be made by "liquiflash" processes.

"Liquiflash" processing involves the use of heat and pressure to reduce the feedstock to a condition in which resistance to flow, e.g., viscosity, which impedes the propensity to form liquid droplets, is eliminated. In this condition, the mass has become liquid or "liquiform." Once all resistance to flow is gone, shear force is applied to the feedstock until discrete particles separate from the mass. The particles, called "shearlite" particles, have a size and shape influenced only by natural mass separation of the flowing feedstock. U.S. Pat. No. 5,458,823 and U.S. application Ser. No. 08/330,412, filed Oct. 28, 1994, both incorporated herein by reference, show processes and devices for such processing.

The inventive compositions may include one or more active ingredients, such as bio-affecting agents. These are typically prescription or over the counter medications.

The bio-affecting agent used may be selected from a broad range of drug, therapeutic or prophylactic materials. Representative classes of drugs include those in the following therapeutic categories: ace-inhibitors; anti-anginal drugs; anti-arrythmia agents; antiasthmatics; anticholesterolemics; anticonvulsants; antidepressants; antidiarrheal preparations; antihistamines; antihypertensives; anti-infectives; anti-inflammatories; antilipid agents; antimaniacs; antinauseants; antistroke agents; antithyroid preparations; anabolic drugs; antiparasitics; antipsychotics; antipyretics; antispasmodics; antithrombotics; anxiolytic agents; appetite stimulants; appetite suppressants; beta-blocking agents; bronchodilators; cardiovascular agents; cerebral dilators; chelating agents; cholecystekinin antagonists; chemotherapeutic agents; cognition activators; contraceptives; coronary dilators; cough suppressants' decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; laxatives; migraine treatments; mineral supplements; mucolytics; narcotics; neuroleptics; neuromuscular drugs; non-steroidal anti-inflammatories (NSAIDs); nutritional additives;

peripheral vasodilators; polypeptides; prostaglandins; psychotropics; renin inhibitors; respiratory stimulants; steroids; stimulants; sympatholytics; thyroid preparations; tranquilizers; uterine relaxants; vaginal preparations; vasoconstrictors; vertigo agents; vitamins; wound healing agents; and others.

Bio-affecting agents which may be used in the invention include: acetaminophen; acetic acid; acetylsalicylic acid, including its buffered forms; albuterol and its sulfate; alcohol; alkaline phosphatase; allantoin; aloe; aluminum acetate; carbonate; chlorohydrate and hydroxide; alprozolam; amino acids; aminobenzoic acid; amoxicillin; ampicillin; amsacrine; amsalog; anethole; ascorbic acid; aspartame; atenolol; bacitracin; balsam peru; BCNU (carmustine); beclomethasone diproprionate; benzocaine; benzoic acid; benzophenones; benzoyl peroxide; bethanechol; biotin; bisacodyl; bornyl acetate; bromopheniramine maleate; buspirone; caffeine; calamine; calcium carbonate, casinate and hydroxide; camphor; captopril; cascara sagrada; castor oil; cefaclor; cefadroxil; cephalexin; cetyl alcohol; cetylpyridinium chloride; chelated minerals; chloramphenicol; chlorcyclizine hydrochloride; chlorhexidine gluconate; chloroxylenol; chloropentostatin; chlorpheniramine maleate; cholestyramine resin; choline bitartrate; chondrogenic stimulating protein; cimetidine and its hydrochloride; cinnamedrine hydrochloride; citalopram; citric acid; clarithromycin; clonidine and its hydrochloride salt; clorfibrate; cocoa butter; cod liver oil; codeine and codeine phosphate; cortisone acetate; ciprofloxacin HCl; cyanocobalamin; cyclizine hydrochloride; danthron; dexbromopheniramine maleate; dextromethorphan hydrobromide; diazepam; dibucaine; diclofenac sodium; digoxin; diltiazem; dimethicone; dioxybenzone; diphenhydramine and its citrate; diphenhydramine hydrochloride; docusate calcium, potassium, and sodium; doxycycline hydrate; doxylamine succinate; efaroxan; enalapril; enoxacin; erythromycin; estropipate; ethinyl estradiol; ephedrine; epinephrine bitartrate; erythropoietin; eucalyptol; famotidine; ferrous fumarate, gluconate and sulfate; folic acid; fosphenytoin; 5-fluorouracil (5-FU); fluoxetine and its hydrochloride; flubiprofen, furosemide; gabapentan; gentamicin; gemfibrozil; glipizide; glycerine; glyceryl stearate; griseofulvin; growth hormone; guafenesin; hexylresorcinol; hydrochlorothiazide; hydrocodone bitartrate; hydrocortisone and its acetate; 8-hydroxyquinoline sulfate; ibuprofen; indomethacin; inositol; insulin; iodine; ipecac; iron; isosorbide and its mono- and dinitrates; isoxicam; ketamine; kaolin; lactic acid; lanolin; lecithin; leuprolide acetate; lidocaine and its hydrochloride salt; lifinopril; liotrix; loratadine; lovastatin; luteinizing hormore; LHRH (lutenizing hormone replacement hormone); magnesium carbonate, hydroxide, salicylate, and trisilicate; mefenamic acid; meclofenamic acid; meclofenamate sodium; medroxyprogesterone acetate; methenamine mandelate; menthol; meperidine hydrochloride; metaproterenol sulfate; methyl nicotinate; methyl salicylate; methyl cellulose; methsuximide; metronidazole and its hydrochloride; metoprotol tartrate; miconazole nitrate; mineral oil; minoxidil; morphine; naproxen and its sodium salt; nifedipine; neomycin sulfate; niacin; niacinamide; nicotine; nicotinamide; nitroglycerine; nonoxynol-9; norethindrone and its acetate; nystatin; octoxynol; octoxynol-9; octyl dimethyl PABA; octyl methoxycinnamate; omega-3 polyunsaturated fatty acids; omeprazole; ondansetron; oxolinic acid; oxybenzone; oxtriphylline; para-aminobenzoic acid (PABA); padimate-O; paramethadione; pentastatin; peppermint oil; pentaerythritol tetranitrate; pentobarbital sodium; pheniramine maleate; phenobarbital; phenol;

phenolphthalein; phenylephrine hydrochloride; phenylpropanolamine and its hydrochloride salt; phenytoin; phenelzine sulfate; pirmenol; piroxicam; polymicin B sulfate; potassium chloride and nitrate; prazepam; procainamide hydrochloride; procaterol; proxephene and its HCl salt; propoxyphene napsylate; pramiracetin; pramoxine and its hydrochloride salt; propanolol HCl; pseudoephedrine hydrochoride and sulfate; pyridoxine; quinapril; quinidine gluconate and sulfate; quinestrol; ralitoline; ranitadine; resorcinol; riboflavin; salicylic acid; sesame oil; shark liver oil; simethicone; sodium bicarbonate, citrate, and fluoride; sodium monofluorophosphate; sucralfate; sulfanethoxazole; sulfasalazine; sulfur; tacrine and its HCl salt; theophylline; terfinidine; thioperidone; trimetrexate; triazolam; timolol maleate; tretinoin; tetracycline hydrochloride; tolmetin; tolnaftate; triclosan; tripolidine hydrochloride; undecylenic acid; vancomycin; verapamil HCl; vidaribine phosphate; vitamins A, B, C, D, $B_1$, $B_2$, $B_6$, $B_{12}$, E, and K; witch hazel; xylometazoline hydrochloride; zinc; zinc sulfate; zinc undecylenate. Mixtures and pharmaceutically acceptable salts of these and other actives can be used.

One group of preferred active ingredients are antacids, $H_2$-antagonists and analgesics.

Antacid dosages can be prepared using ingredients such as: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, calcium carbonate, calcium phosphate, citrate ion (acid or salt), amino acetic acid, hydrate of magnesium aluminum sulfate, magaldrate, magnesium aluminosilicate, magnesium carbonate, magnesium glycinate, magnesium hydroxide, magnesium oxide, magnesium trisilicate, milk solids, aluminum mono- or di-basic calcium phosphate, tricalcium phosphate, potassium bicarbonate, sodium tartrate, sodium bicarbonate, magnesium aluminosilicates, tartaric acids and salts, and the like. Mixtures are operable. Moreover, antacids can be used in combination with $H_2$-antagonists.

Chewable antacid compositions which dissolve quickly can be made using the compositions of the invention.

Preferred analgesics include aspirin, acetaminophen, acetaminophen plus caffeine, and ibuprofen.

Other useful active ingredients include antidiarrheals such as IMMODIUM AD; antihistamines; antitussives; decongestants; vitamins and breath fresheners. Also contemplated are anxiolytics such as XANAX; antipsychotics such as CLOZARIL and HALDOL; non-steroidal antiinflammatories, such as VOLTAREN AND LODINE; antihistamines such as SELDANE, HISMANAL, RELAFEN and TAVIST; antiemetics such as KYTRIL and CESAMET; bronchodilators such as BENTOLIN, PROVENTIL; antidepressants such as PROZAC, ZOLOFT, and PAXIL; antimigraine agents such as IMIGRAN; ace-inhibitors such as VASOTEC, CAPOTEN AND ZESTRIL; anti-Alzheimers agents such aas NICERGOLINE; and $Ca^{II}$-antagonists such as PROCARDIA, ADALAT AND CALAN.

H$_2$-antagonists contemplated include cimetidine, ranitidine hydrochloride, famotidine, nizatidine, ebrotidine, mefentidine, roxatidine, pisatidine and aceroxatidine.

Other ingredients which may be included are fillers, fragrances, dyes, flavors, sweeteners (both artificial and natural), and other conventional tablet additives.

For example, fillers may be used to increase the bulk of the tablet. Some of the commonly used fillers are calcium sulfate, both di- and tri-basic; starch; calcium carbonate; microcrystalline cellulose; modified starches, lactose, sucrose; mannitol and sorbitol.

Flavors may be chosen from natural and synthetic flavoring liquids. An illustrative list of such agents includes volatile oils, synthetic flavor oils, flavoring aromatics, oils, liquids, oleoresins and extracts derived from plants, leaves, flowers, fruits, stems and combinations thereof. A non-limiting representative list of these includes citric oils, such a lemon, orange, grape, lime and grapefruit an fruit essences, including apple, pear, peach, grape, strawberry, raspberry, cherry, plum, pineapple, apricot, or other fruit flavors.

Other useful flavorings include aldehydes and esters, such as benzaldehyde (cherry, almond); citral, i.e., alpha-citral (lemon, lime); neral, i.e., beta-citral (lemon, lime); decanal (orange, lemon); aldehyde C-8 (citrus fruits); aldehyde C-9 (citrus fruits); aldehyde C-12 (citrus fruits); tolyl aldehyde (cherry, almond); 2,6-dimethyloctanal (green fruit); 2-dodedenal (citrus, mandarin); mixtures thereof and the like.

The sweeteners may be chosen from the following non-limiting list: glucose (corn syrup), dextrose, invert sugar, fructose, and mixtures thereof (when not used as a carrier); saccharin and its various salts, such as the sodium salt; dipeptide sweeteners such as aspartame; dihydro-chalcone compounds, glycyrrhizin; *Stevia Rebaudiana* (Stevioside); chloro derivatives or sucrose such as sucralose; and sugar alcohols such as sorbitol, mannitol, xylitol, and the like. Also contemplated are hydrogenated starch hydrolysates and the synthetic sweeteners such as 3,6-dihydro-6-methyl-1-1-1,2,3-oxathiazin-4-one-2,2-dioxide, particularly the potassium salt (acesulfame-K), and sodium and calcium salts thereof. Other sweeteners may also be used.

Some embodiments include an effervescent disintegration agent to aid in masking the objectional taste of active ingredients, such as vitamins, medicines and/or minerals, etc. The positive organoleptic sensation achieved by the effervescent action in the mouth, as well as the texture, speed and sensation of disintegration, aid in masking undesirable flavor notes.

"Effervescent" refers to those agents which evolve gas. The gas- or bubble-generating action is often the result of the reaction of a soluble acid source and a carbonate source. The reaction of these two general classes of compounds produces carbon dioxide gas upon contact with water in saliva. Useful acids include: citric, tartaric, malic, fumaric, adipic, succinic and acid salts and anhydrides thereof. Acid salts may also include sodium dihydrogen phosphate, disodium dihydrogen pyrophosphate, acid citrate salts and sodium acid sulfite. While the food acids can be those indicated above, acid anhydrides of the above-described acids may also be used. Carbonate sources include dry solid carbonate and bicarbonate salts such as sodium bicarbonate, sodium carbonate, potassium bicarbonate and potassium carbonate, magnesium carbonate and sodium sesquicarbonate, sodium glycine carbonate, L-lysine carbonate, arginine carbonate and amorphous calcium carbonate. Mixtures of various acid and carbonate sources, as well as other sources of effervescence, can be used.

The effervescent agent can be included in at least three different ways. The first method includes incorporating the entire effervescent agent in the feedstock which is used to form the shearform product. The second involves adding the agent to an already formed shearform matrix. The third method incorporates one portion of the agent in the shearform matrix and adds another portion after formation of the matrix material. The artisan can determine the best way to use the agent for its effervescent properties.

Other ingredients include binders which contribute to the ease of formation and general quality of the tablet. Binders include starches, pregelatinized starches, gelatin, polyvinylpyrrolidone, methylcellulose, sodium carboxymethylcellulose, ethylcellulose, polyacrylamides, polyvinyloxoazolidone and polyvinylalcohols.

Color additives can be used in preparing tablets. Such color additives include food, drug and cosmetic colors (FD&C), drug and cosmetic colors (D&C) or external drug and cosmetic colors (Ext. D&C). These colors are dyes, lakes, and certain natural and derived colorants. Useful lakes include dyes absorbed on aluminum hydroxide or other suitable carriers.

An optional feature involves microspheres which are components of substrate/coating systems. The substrate can be a non-active ingredient, such as a saccharide-based material, or it can be an active or a combination of actives. In one embodiment, the substrates are sugar shearlite particles having active agents coated thereon. The coating may include other types of coating materials, e.g., coloring agents. Additional coatings can be used.

Other useful substrate/coating systems employ substrates which are shearlite particles of one or more actives. Coatings thereon can contain saccharides and other ingredients.

Controlled release coatings, e.g., sustained release coatings, are among the preferred types of coatings for use in dosage forms which include bio-affecting agents.

Using the invention, strong, highly attractive dosage units, e.g., tablets, can be produced having textures and internal structures which are relatively open to solubilization. Applicants' compositions are intended generally formed into tablets at pressures of from about 500 up to about 6,000 psi. These tablets have initial hardness values of about 0.5 to about 5.0 lbs.

The following non-limiting examples illustrate the invention.

EXAMPLES

Example I

Ibuprofen Microspheres

Ibuprofen was processed into spheres as follows:

An ibuprofen powder feedstock was fed to the 5-inch spinning head disclosed in U.S. patent application Ser. No. 08/874,215 filed on Jun. 13, 1997, entitled A SPINNER HEAD HAVING FLOW RESTRICTING INSERTS. The head was rotated at about 3600 rpm while the heating elements were raised to a temperature which produced the liquiflash conditions. The feedstock also contained 10% Compritol 888 ATO and 2% Gelucire 50/13. (Compritol 888 ATO is glycerol behenate NF, a lipophilic additive from Gattefosse S. A., a French company. Gelucire, a polyethylene glycol 32 glyceryl ester solubility enhancer, is also available from Gattefosse.)

The spinning head forced the material through the screen and the product was permitted to free fall a distance of from 6 to 8 feet below the head. The product consists of spheres having a highly consistent particle size, with diameters ranging from about 50 to 200 microns.

The product was subjected to testing to determine the time required for dissolution of the active ingredient. The monograph is provided by the U.S. Pharmacopeial Convention, Inc. In the U.S. Pharmaceopoeial National Formulary Monograph for Ibuprofen Dissolution Study, U.S. 23 NF 18, page 786 (1995). At a composition level of 88% ibuprofen, the time for dissolution of most of the ibuprofen was about 15 minutes. Virtually total dissolution occurred at around 20 to 25 minutes. These results show high predictability for delivery using these microspheres.

The microspheres can be caoted with taste masking coatings containing ethyl acrylate and methyl methacrylate polymers and hydroxypropyl methylcellulose polymers.

Example II

Acetaminophen Microspheres

Acetaminophen powder (melting point 169°–170.5° C.) was made into microspheres using a procedure similar to that described in Example I. Fine spheres, all smaller than about 420 microns in diameter, were formed. The spheres were coated with ethyl cellulose polymers and hydroxypropyl cellulose polymers for tast masking.

Example III

Unifloss

Using a procedure similar to that of Example I, ibuprofen (IBP) microspheres were made from a formulation containing 88% ibuprofen, 10% Compritol and 2% Gelucire.

A mixture of 78.25% sucrose, 11.0% sorbitol, 10.0% xylitol and 0.75% TWEEN 80 was prepared. Two kilograms of this material was spun into a floss at 250° C. using 60 Hz head speed. 0.052 kg of ethanol was mixed with the floss, yielding a floss that was recrystallized from about 5% to about 30%. It was dried and granulated to 20 mesh size.

The microspheres and floss were then admixed used in the following composition:

| COMPOSITION | PERCENTAGE |
| --- | --- |
| IBP MICROSPHERES | 34.4% |
| FLOSS | 62.7% |
| CITRIC ACID | 0.7% |
| LEMON FLAVOR | 0.4% |
| WHIPPED CREAM FLAVOR | 0.3% |
| SYLOID 244 FP | 0.5% |
| SODIUM STEARYL FUMARATE | 1.0% |

Using a Kilian T-200 press, tablets having an average weight of about 750 mg were pressed to a 2 lb. initial hardness (up to 8,000 psi) by placing the floss mix in the equipment hopper.

Example IV

Reduced Xylitol Floss

Using the procedure of Example I, ibuprofen microspheres were made from a formulation containing 88% ibuprofen, 10% Compritol and 2% Gelucire. Via a single floss process similar to that of Example VI, a floss was made from the following composition: 83.25% sucrose, 11.0% sorbitol, 5.0% xylitol and 0.75% TWEEN.

The microspheres and floss were used in the following composition:

| COMPOSITION | PERCENTAGE |
| --- | --- |
| IBP MICROSPHERES | 34.4% |
| FLOSS | 62.7% |
| CITRIC ACID | 0.7% |
| LEMON FLAVOR | 0.4% |
| WHIPPED CREAM FALVOR | 0.3% |
| SYLOID 244 FP | 0.5% |
| SODIUM STEARYL FUMARATE | 1.0% |

The ingredients were mixed and the mix was tableted using procedures as described in Example III.

Example V

Acetaminophen Tablets

Using a procedure similar to that employed in Example I, acetaminophen (APAP) microspheres were made from a formulation containing 90% APAP, 7.5% carnauba wax, and 2.5% Pluronic F68. The spheres were then coated with a 45:55 mixture of ethyl cellulose and hydroxypropyl cellulose.

Using the procedure shown in Example III, a unifloss was made containing 78.25% sucrose, 11.00% sorbitol, 10.00% xylitol and 0.75% Tween 80. The floss was chopped in the presence of 2% lactose and granulated after the addition of 0.5% ethanol.

Tablets were made from the following composition:

| COMPOSITION | PERCENTAGE |
| --- | --- |
| IBP MICROSPHERES | 46.22% |
| FLOSS | 48.68% |
| GRAPE FLAVOR | 0.70% |
| CITRIC ACID | 0.30% |
| MANNITOL | 2.00% |
| SYLOID | 0.10% |
| ADIPIC ACID | 2.00% |

Using a Kilian T200 press, 500 mg tablets were pressed to a 2 lb. initial hardness (compaction pressures up to 8000 psi) by placing the composition in the feed hopper and allowing gravity to feed the dies.

Example VI

Cimetidine Tablets

Using procedures set out in Example V, microspheres and floss were made from the following compositions:

| MICROSPHERES | |
| --- | --- |
| COMPOSITION | PERCENTAGE |
| CIMETIDINE | 40% |
| MYVATEX | 50% |
| PLURONIC F68 | 10% |

The microspheres were coated for taste masking with ethyl cellulose and hydroxypropylcellulose.

| FLOSS | |
|---|---|
| COMPOSITION | PERCENTAGE |
| SUCROSE | 83.25% |
| SORBITOL | 11.00% |
| XYLITOL | 5.00% |
| TWEEN 80 | 0.75% |

The following formulation was mixed and tableted:

| COMPOSITION | PERCENTAGE |
|---|---|
| CIMETIDINE BEADS | 33.90% |
| FLOSS | 63.80% |
| LEMON FLAVOR | 0.60% |
| ASPARTAME | 0.60% |
| CITRIC ACID | 1.00% |
| SYLOID | 0.10% |

Using a Kilian T200 press, 750 mg tablets were pressed to a 2 lb. initial hardness.

Example VII

Vitamin C Tablets

Using the unifloss from Example III a fast dissolving vitamin C tablet was made. The tablet composition contained:

| COMPOSITION | PERCENTAGE |
|---|---|
| DESCOTE COATED ASCORBIC ACID | 30.77% |
| FLOSS | 62.75% |
| MANNITOL | 3.00% |
| ADIPIC ACID | 2.00% |
| ORANGE FLAVOR | 1.00% |
| SYLOID | 0.30% |
| MONOAMMONIUM GLYCERRHIZATE | 0.03% |
| FD&C YELLOW #6 LAKE | 0.15% |

650 mg tablets, having 2 to 4 lb. hardness, were made.

There have been described what are presently believed to be the preferred embodiments of the invention. Those skilled in the art will realize that changes and modifications may be made thereto without departing from the spirit of the invention, and it is intended to claim all such changes and modifications as fall within the true scope of the invention.

What is claimed is:

1. A flowable particulate composition for making dosage units comprising:
   a) at least one flowable, partially crystallized amorphous matrix, said matrix comprising at least one carbohydrate and at least one sugar alcohol;
   b) a bio-affecting agent in the form of a coated or uncoated particle; and
   c) a tableting aid.

2. The composition of claim 1 wherein the at least one matrix comprises one flowable, partially crystallized amorphous matrix comprising at least one carbohydrate and a mixture of sugar alcohols.

3. The composition of claim 1 wherein the at least one matrix further comprises at least one crystallization modifier.

4. The composition of claim 1 wherein the matrix comprises sucrose, xylitol and sorbitol.

5. The composition of claim 1 wherein said partially crystallized matrix is from about 5% to about 20% partially crystallized.

6. The composition of claim 1 wherein said bio-affecting agent is in the form of microspheres.

7. The composition of claim 6 wherein said bio-affecting agent is selected from the group consisting of anti-inflammatories, antacids, and $H_2$ antagonists.

8. The composition of claim 3 wherein the crystallization modifier is selected from the group consisting of lecithin, polyethylene glycol, propylene glycol, and polyoxyethylene sorbitan fatty acid esters.

9. The composition of claim 1 in the form of a compressed tablet that dissolves in the mouth in less than 30 seconds.

10. A process for preparing a dissolve in the mouth tablet comprising:
   a) preparing at least one amorphous matrix, said matrix comprising at least one carbohydrate and at least one sugar alcohol;
   b) combining said at least one amorphous matrix with a bio-affecting agent, said agent in the form of a coated or uncoated particle;
   c) partially crystallizing said matrix prior to or after mixing said matrix with said bio-affecting agent;
   d) placing said partially crystallized matrix and bio-affecting agent mix into a tablet press supply hopper or container;
   e) transporting said mix from said hopper or container to a tablet press die by means of gravity or vacuum;
   f) compressing said transported mix into a tablet or dosage unit at compaction pressures of from about 500 psi to about 10,000 psi; and
   g) aging said tablet or dosage unit to fully crystallize the matrix.

11. A rapid dissolve tablet which dissolves in the mouth, with or without water, in from about 3 seconds to about 30 seconds, said tablet comprising:
   a) a crystallized matrix comprising a carbohydrate and at least one sugar alcohol; and
   b) a particulate bio-affecting agent.

12. The composition of claim 1 wherein said partially crystallized amorphous matrix is from about 5% to about 30% crystallized.

13. The composition of claim 12 wherein the partial crystallization is effected by contacting the matrix with ethanol.

14. A process for preparing a dosage unit comprising:
   (A) preparing at least one amorphous matrix comprising at least one carbohydrate and at least one sugar alcohol;
   (B) combining said matrix with at least one bio-affecting agent, which bio-affecting agent may be coated or uncoated;
   (C) partially crystallizing said matrix with a crystallization modifier prior to or after mixing same with said bioaffecting agent;
   (D) placing the mix of step (C) into a tablet press supply hopper or a container;
   (E) compressing the mix to form at least one dosage unit; and
   (F) aging said dosage unit to fully crystallize said matrix.

15. The composition of claim 1 wherein the crystallization modifier is ethanol.

* * * * *